US010442701B2

(12) United States Patent
Uno

(10) Patent No.: US 10,442,701 B2
(45) Date of Patent: Oct. 15, 2019

(54) WATER TREATING METHOD, WATER TREATING APPARATUS, AND CAVITATION GENERATION RING

(71) Applicant: ECO PRANA CO., LTD., Hyogo (JP)

(72) Inventor: Kaoru Uno, Hyogo (JP)

(73) Assignee: Eco Prana Co., Ltd., Hyogo (JP)

( * ) Notice: Subject to any disclaimer, the term of this patent is extended or adjusted under 35 U.S.C. 154(b) by 486 days.

(21) Appl. No.: 15/128,832

(22) PCT Filed: Mar. 25, 2014

(86) PCT No.: PCT/JP2014/058207
§ 371 (c)(1),
(2) Date: Sep. 23, 2016

(87) PCT Pub. No.: WO2015/145563
PCT Pub. Date: Oct. 1, 2015

(65) Prior Publication Data
US 2017/0113946 A1 Apr. 27, 2017

(51) Int. Cl.
*C02F 1/34* (2006.01)
*C02F 1/00* (2006.01)
(Continued)

(52) U.S. Cl.
CPC .............. *C02F 1/005* (2013.01); *A01N 37/08* (2013.01); *B01F 3/0446* (2013.01); *B01F 3/04503* (2013.01); *B01F 3/04978* (2013.01); *B01F 5/061* (2013.01); *B01F 11/0283* (2013.01); *C02F 1/34* (2013.01); *C02F 1/68* (2013.01);
(Continued)

(58) Field of Classification Search
CPC .... B01F 3/0446; B01F 3/0865; B01F 5/0415; B01F 5/0451; B01F 5/061; B01F 5/0618; B01F 5/0646; B01F 2005/0441; B01F 2005/0621; B01F 2005/0636; B63B 13/00;
(Continued)

(56) References Cited
U.S. PATENT DOCUMENTS 6,030,535 A * 2/2000 Hayashi ................. B01D 61/58
210/652
2004/0251566 A1* 12/2004 Kozyuk ................. B01F 3/0446
261/76
(Continued)

FOREIGN PATENT DOCUMENTS

JP 11-262754 A 9/1999
JP 2003-180158 A 7/2003
(Continued)

*Primary Examiner* — Walter D. Griffin
*Assistant Examiner* — Cameron J Allen
(74) *Attorney, Agent, or Firm* — Muncy, Geissler, Olds & Lowe, P.C.

(57) ABSTRACT

A water treating method includes a step of installing a cavitation generation ring in a part of a water communication pipe, and a step of passing water through the inside of the cylindrical portion at high pressure, thereby cavitation being generated in the cylindrical portion and clusters of molecules of water being fined. A cavitation generation ring is configured to be installed in a part of a water communication pipe. A water treating apparatus includes a cavitation generation ring, a water communication pipe and a pressurizing pump for water.

11 Claims, 5 Drawing Sheets

(51) Int. Cl.
*B01F 5/06* (2006.01)
*B01F 3/04* (2006.01)
*A01N 37/08* (2006.01)
*B01F 11/02* (2006.01)
*C02F 1/68* (2006.01)
*C02F 103/02* (2006.01)

(52) U.S. Cl.
CPC ............... *B01F 2005/0636* (2013.01); *B01F 2215/0052* (2013.01); *C02F 2103/026* (2013.01)

(58) Field of Classification Search
CPC ... B63J 4/002; B63J 4/004; C02F 1/78; C02F 1/34; C02F 1/722; C02F 2103/008
See application file for complete search history.

(56) References Cited

U.S. PATENT DOCUMENTS

2010/0032354 A1* 2/2010 Uematsu ............... B01F 3/0446
                                                            210/150
2010/0276820 A1 11/2010 Mogami et al.

FOREIGN PATENT DOCUMENTS

| | | |
|---|---|---|
| JP | 2003-200156 A | 7/2003 |
| JP | 2006-181449 A | 7/2006 |
| JP | 2008-161819 A | 7/2008 |
| WO | WO 2009/088085 A1 | 7/2009 |

\* cited by examiner

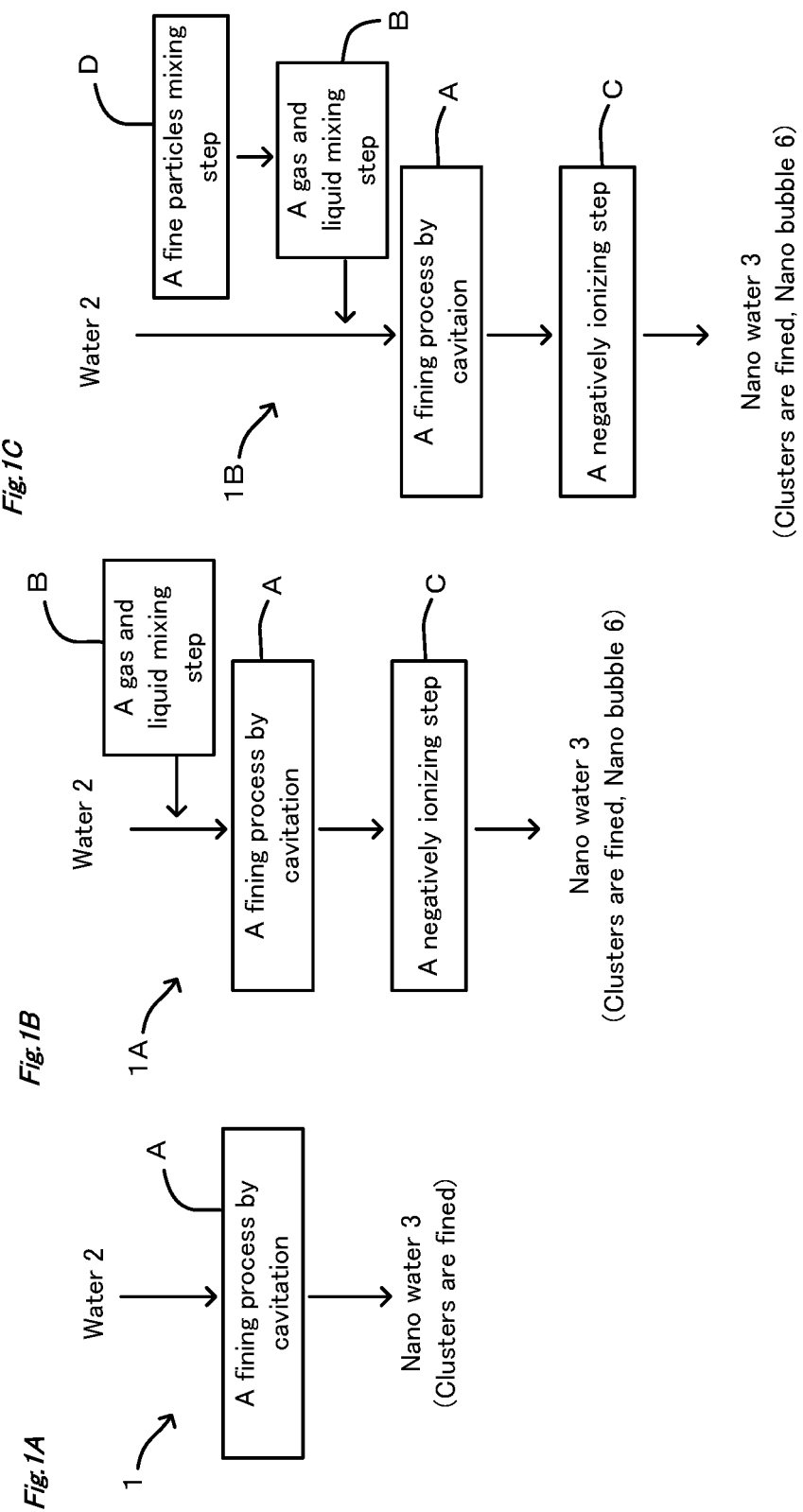

WATER TREATING METHOD, WATER TREATING APPARATUS, AND CAVITATION GENERATION RING

TECHNICAL FIELD

The present invention relates to a water treating method, a water treating apparatus, and a cavitation generation ring.

BACKGROUND ART

Various methods for fining the clusters of molecules of water have been proposed.

For instance, Patent Literature 1 below discloses a water treating method and a water treating apparatus, characterized in that a high pressure water jet is injected into the water flowing in a water channel to generate cavitation and fine the clusters of molecules of water.

The water treating method and the water treating apparatus are characterized in that a magnetic field is acted on the electric conductive vacuum microbubbles which are generated by cavitation to generate a force based on the Fleming's left-hand rule, then the clusters of the water molecules around the vacuum microbubbles are fined by this force.

CITING LIST

Patent Literature

PLT 1: Japanese Patent Publication (unexamined) No. 2006-181449-A

SUMMARY OF INVENTION

Technical Problem

However, the water treating method and water treating apparatus require the usage of an apparatus for generating a magnetic field for fining the clusters of water molecules, therefore the method is complicated and a large scale apparatus is required, so more improvements are needed.

The present invention is proposed in view of the above mentioned problems. The present invention has an object to provide a water treating method, a water treating apparatus and a cavitation generation ring, which fine the clusters of water molecules by a simple method.

Solution to Problem

In order to achieve the above-mentioned objects, a water treating method of one embodiment of the present invention is characterized in that the water treating method, having a step of installing a cavitation generation ring in a part of a water communication pipe, the cavitation generation ring having a cylindrical portion and a plurality of protrusions, inside the cylindrical portion a water communication path being formed, the plurality of protrusions protruding toward a center from an inner peripheral surface of the cylindrical portion; and a step of passing water through the inside of the cylindrical portion at high pressure, thereby cavitation being generated in the cylindrical portion and clusters of molecules of water being fined.

The present invention can further include a gas and liquid mixing step for containing a lot of gas bubbles in the water by mixing a gas into the water communication pipe to an upstream side of the cavitation generation ring, wherein cavitation is generated in the cylindrical portion by passing the water containing the gas bubbles through the inside of the cylindrical portion at high pressure, thereby the clusters of molecules of the water are fined and also the gas bubbles are fined in Nano-size.

And the present invention can further include a fine particles mixing step for mixing and dispersing fine particles in Nano-size in the gas in the gas and liquid mixing step, before the gas is mixed into the water in the gas bubbles fined in Nano-size, thereby the fine particles being enclosed.

And the present invention can be characterized in that the fine particles are made by drying and powdering an extract of stevia stem and fining the powdered extract in Nano-size.

And the present invention can further include a negatively ionizing step for having the water which contains the gas bubbles fined in Nano-size by the cavitation pass through the inside of a magnetic mixer, thereby the gas bubbles being negatively ionized.

In addition, in order to achieve the above-mentioned objects, a cavitation generation ring of one embodiment of the present invention is characterized in that the cavitation generation ring is configured to be installed in a part of a liquid communication pipe, having a cylindrical portion and a plurality of protrusions, inside the cylindrical portion a water communication path being formed, the plurality of protrusions protruding toward a center from an inner peripheral surface of the cylindrical portion, wherein water is made to pass through the inside of the cylindrical portion at high pressure, thereby cavitation is generated in the cylindrical portion and clusters of molecules of the water are fined and gas bubbles contained in the water are fined in Nano-size.

In addition, in order to achieve the above-mentioned objects, a water treating apparatus of one embodiment of the present invention is characterized in that the water treating apparatus includes the cavitation generation ring in the above embodiment, a water communication pipe and a pressurizing pump for water.

And the present invention can further include a gas and liquid mixing apparatus for containing a lot of gas bubbles in the water by mixing gas into the water communication pipe to an upstream side of the cavitation generation ring.

And the present invention can further include an apparatus for mixing fine particles, the apparatus mixing and dispersing fine particles in Nano-size in the gas, before the gas is mixed into the water by the gas and liquid mixing apparatus.

And the present invention can be characterized in that the fine particles are made by drying and powdering an extract of stevia stem and fining the powdered extract in Nano-size.

And the present invention can further include a plurality of the cavitation generation rings which are able to be mutually connected and separated, wherein amount of cavitation generation can be adjusted by increasing or decreasing the number of the connected cavitation generation rings.

And the present invention can be characterized in that each of the plurality of protrusions of the cavitation generation rings has a mushroom shape and the cavitation generation ring has a combination of head portions in two or more different sizes.

Advantageous Effects of Invention

The preset invention, i.e. the water treating method, the water treating apparatus, and the cavitation generation ring, fine the cluster of molecules of water by a simple method.

BRIEF DESCRIPTION OF DRAWINGS

FIG. 1 A, FIG. 1 B and FIG. 1 C are flow charts showing an example of the water treating method in an embodiment of the present invention. FIG. 1 A shows the first embodiment, FIG. 1 B shows the second embodiment and FIG. 1 C shows the third embodiment.

FIG. 2 A is a schematic plan view. FIG. 2 B is a schematic longitudinal sectional view taken in the direction of the arrows substantially along the line X-X in FIG. 2 A.

FIG. 3 A is a schematic plan view. FIG. 3 B is a schematic longitudinal sectional view taken in the direction of the arrows substantially along the line Y-Y in FIG. 3 A.

FIG. 4 B is a schematic view showing Nano bubbles after cavitation treatment.

FIG. 5 A shows the first embodiment, FIG. 5 B shows the second embodiment and FIG. 5 C shows the third embodiment.

DESCRIPTION OF EMBODIMENTS

As shown in FIG. 1 A, a water treating method 1 in the first embodiment of the present invention has a fining process A for fining clusters of molecules of water 2 by cavitation to generate Nano water 3.

Figure 5A:
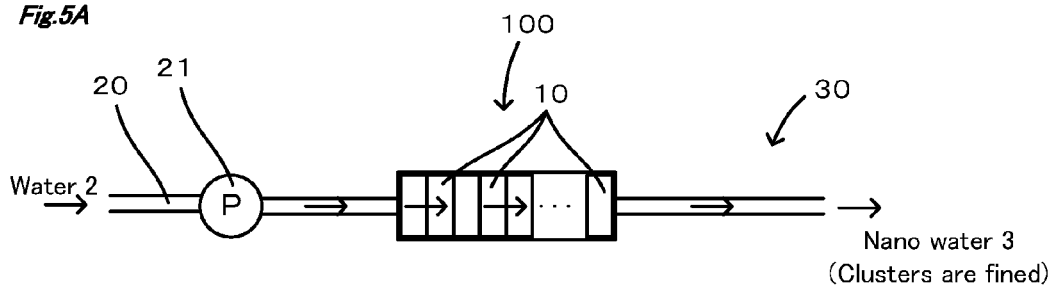
FIGS. 5 A-5 C are a schematic view showing an example of the water treatment apparatus in an embodiment of the present invention.
Figure 5B:
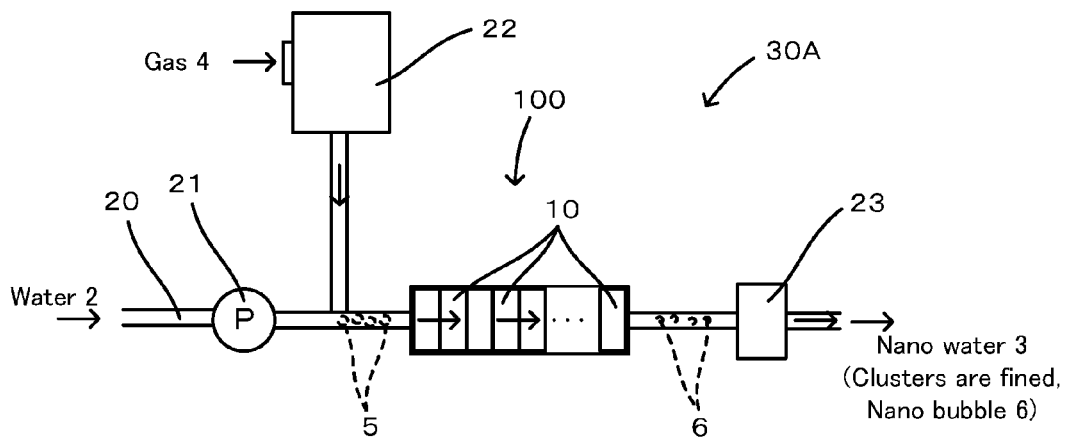
Figure 5C:
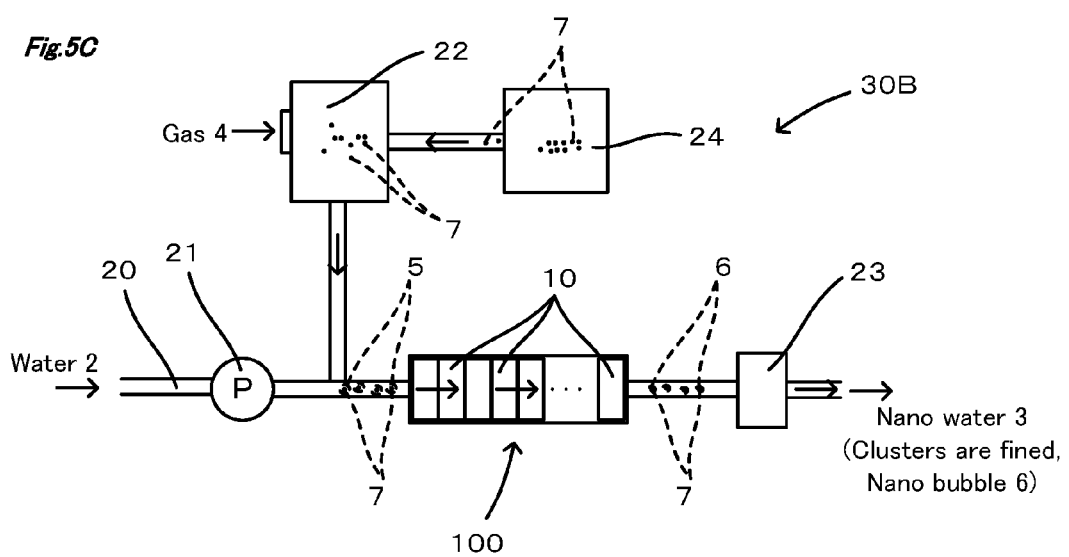

As shown in FIG. 5 A, the fining process A is executed by a water treating apparatus 30 which has a fining apparatus 100 having a plurality of cavitation generation rings 10 (hereinafter, referred to as rings 10), a water communication pipe 20 and a pressurizing pump 21 for the water 2.

In this fining process A, water 2 is made to pass through the ring 10 (the fining apparatus 100) which is installed in a part of the water communication pipe 20 at high pressure with the pressurizing pump 21, then cavitation is generated in the ring 10, and the clusters of molecules of the water 2 are fined by the cavitation and the Nano water 3 is generated.

The water 2 is constituted with water molecules gathering together, and generally speaking, in the water 2, a lot of water molecules form a group (a cluster of water molecules) by hydrogen bonds, and for example, in tap water, clusters of water molecules are formed, each cluster being constituted with 15 to 20 water molecules gathering together.

And generally speaking, the water containing clusters in small size has a high permeating capability, therefore it brings about various kinds of beneficial effects for human, animals and plants etc. from a physiological and a medical perspectives.

By the water treating method 1 and the water treating apparatus 30 composed as mentioned above, the water 2 is affected by cavitation, then the size of clusters become small and the Nano water 3 is generated, which contains about 2 to 5 water molecules on an average, and has a high permeating capability.

"Nano water 3" in this specification means the water in which clusters are fined and "Nano" is a term conceptually expressing a fined object.

The Nano water 3 is effectively absorbed via skin, intestine or cell surface etc., so cells are activated, therefore there are various kinds of usages of the Nano water 3, such as drinking water, hydroponics of plants, rearing of tropical fish, cosmetics related to beauty.

If the Nano water 3 is used as a drinking water, it improves one's health; if used for hydroponics of plants or rearing of tropical fish, it accelerates the growth of plants or tropical fish; if used for cosmetics etc., the Nano water 3 is effectively permeated via skin etc.

Figure 2A:
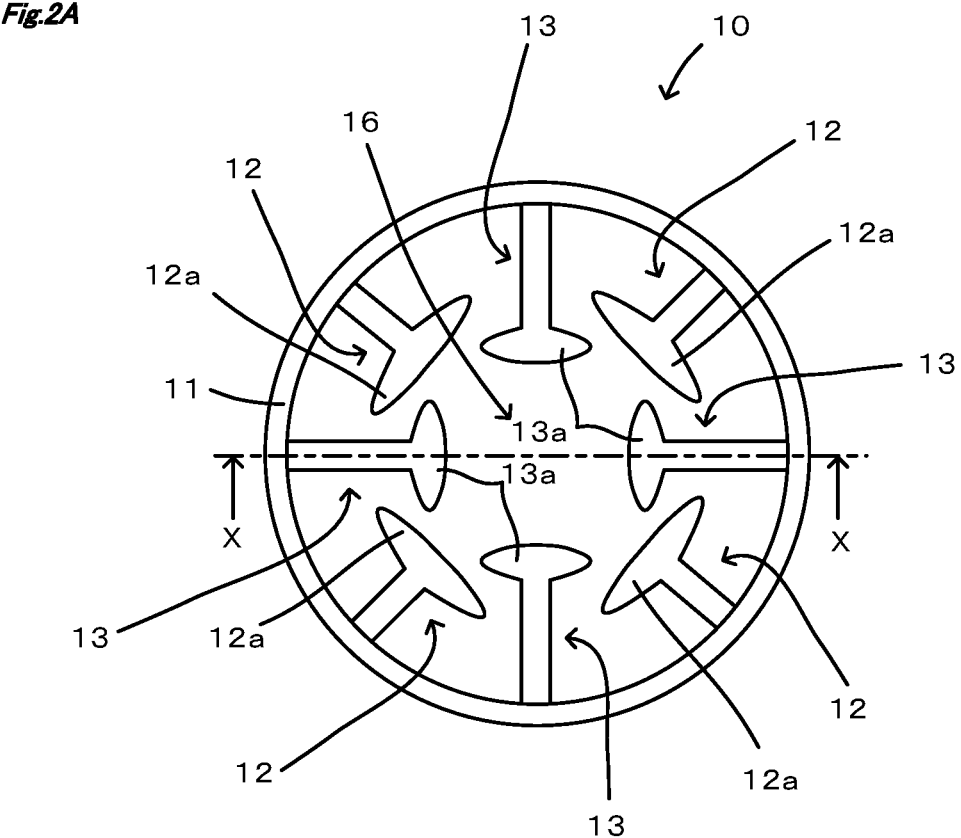
FIGS. 2 A-2 B show an example of the cavitation generation ring for an embodiment of the present invention schematically.
Figure 2B:
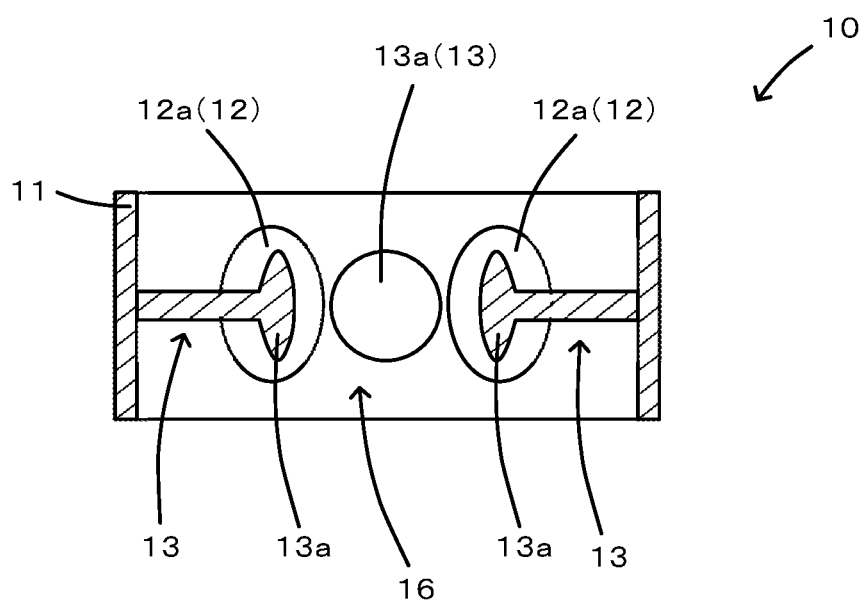

As shown in FIGS. 2 A and 2 B, the ring 10 which is used for the water treating method 1 and the water treating apparatus 30 has a cylindrical portion 11 and a plurality of protrusions 12,13, inside the cylindrical portion 11 a water communication path 16 being formed, the plurality of protrusions 12,13 protruding toward a center from an inner circumference of the cylindrical portion 11.

In this embodiment, the ring 10 has a plurality of protrusions 12 having the substantially same size and shape (four protrusions are shown in the figure), and has a plurality of protrusions 13 (four protrusions are shown in the figure), and the projecting dimension of the protrusion 13 is larger than that of the protrusion 12.

When the water 2 is made to pass through the inside of the cylindrical portion 11 of the ring 10 composed as mentioned above at high pressure with the pressurizing pump 21, the water 2 collides with the protrusions 12,13 while it goes through the water communication path 16 of the cylindrical portion 11, then the pressure of the water around the portion of the protrusions 12,13 colliding the water 2 is instantly decreased.

When the pressure of water becomes lower than the saturated steam pressure for only a short time like this, the water 2 starts to boil with minute bubble-nuclei as nuclei, the nuclei existing in the water 2 and each smaller than 100 micrometers, or dissolved gas is released, thereby a lot of small bubbles (vacuum microbubbles) are formed.

The pressure of the water 2 around these vacuum microbubbles is higher than the saturated steam pressure, therefore the water 2 around the vacuum microbubbles rush toward a center of the vacuum microbubbles and at the moment when the vacuum microbubbles are collapsed, the water 2 rushes to and collides at a center, thereby a strong pressure wave (shock wave) is generated and cavitation is generated inside the cylindrical portion 11.

This strong shock wave based on the cavitation acts on the clusters of the water molecules surrounding the vacuum microbubbles and part of the hydrogen bonds are cut and as a result, the clusters are collapsed (fined) to be clusters in small size, then the Nano water 3 is generated.

In this embodiment, as shown in FIGS. 2 A and 2 B, each of the plurality of protrusions 12,13 of the ring 10 has a mushroom shape and has a combination of head portions 12a,13a in two or more different sizes. In the figure, the head portions 12a,13a having substantially disk shapes are shown and the ring 10 having two kinds of head portions 12a,13a is shown.

By combining the head portions 12a,13a having more than two kinds of sizes like this, the above mentioned shock wave is effectively generated and the effect of cavitation is enhanced, therefore the clusters of the water 2 are more effectively fined. The sizes of the head portions 12a, 13a can be set as those which do not interfere with each of the protrusions 12, 13. The sizes of the head portions 12a,13a are not limited to those in the figures, the head portions in different sizes, for example, three or four sizes can be used.

In this embodiment, as shown in FIG. 5A, the fining apparatus 100 is constituted with a plurality of connected rings 10, which are able to be connected to and separated from each other. These multiple rings 10 are connected in such a manner that the inside spaces of cylinders communicate to form the fining apparatus 100. Because of the above structure, the amount of cavitation is increased or decreased by increasing or decreasing the number of the connected rings 10 appropriately constituting the fining apparatus 100. If the number of the connected rings 10 is increased, the amount of cavitation generation is increased and the region where the above mentioned shock wave is generated is widened, therefore the degree of fining the clusters is enhanced. On the other hand, if the number of the connected rings 10 is decreased, the degree of fining the clusters is decreased.

That is to say, by adjusting the amount of the cavitation generation like this, the degree of fining the clusters of the water 2 is adjusted, therefore the Nano water 3 which has a desired permeation capability is obtained.

As the pressurizing pumps 21, those which pass the water 2 through the inside of the water communication pipes 20 at high pressure can be used, and those having various structures can be used. As the water communication pipes 20, those which are durable for the circulation of the water 2 at high pressure can be used, and those which are made from metal, e.g., iron, copper, or those which are made from synthetic resin, e.g., a polyvinyl chloride resin can be used.

The pressure of the water 2 passing through the inside of the ring 10 can be in a range from about 1 to 10 MPa, and the flow speed of the water 2 can be 150 m/min (meter/minute) or over. The pressure and the flow speed of the water 2 can be appropriately adjusted for generating effective cavitation, for example, they can be adjusted according to the temperature of the water 2 etc.

The inside diameter of the cylindrical part 11 of the ring 10 can be, for example, in a range from 10 to 50 mm, and the width dimension (dimension along the flow direction of the water 2) of the cylindrical part 11 can be, for example, in a range from 5 to 30 mm. The projection dimension of the protrusions 12,13 can be set so that the protrusions 12,13 do not interfere with each other, for example, can be set in a range from about 1/10 to 1/2 in a dimension of the inside diameter of the cylindrical part 11.

As the rings 10, those which are made from ceramic of oxide etc. such as aluminum oxide, zirconia can be used, or those which are made from metal such as stainless steel or those which are made from synthetic resin etc. can be used. If the rings 10 are made from ceramic, the hydrogen bonds between the molecules of the water 2 passing through the inside of the ring 10 are weakened by the effect of far-infrared ray radiated from ceramic, thereby the clusters are easily fined.

Figure 3A:
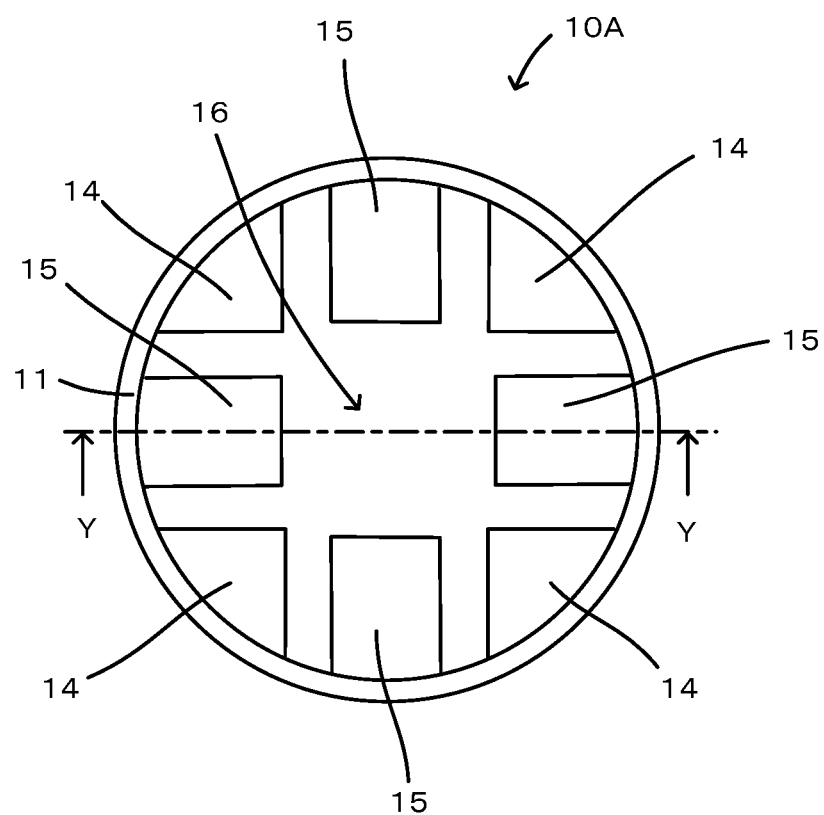
FIGS. 3 A-3 B show another example of the cavitation generation ring schematically.
Figure 3B:
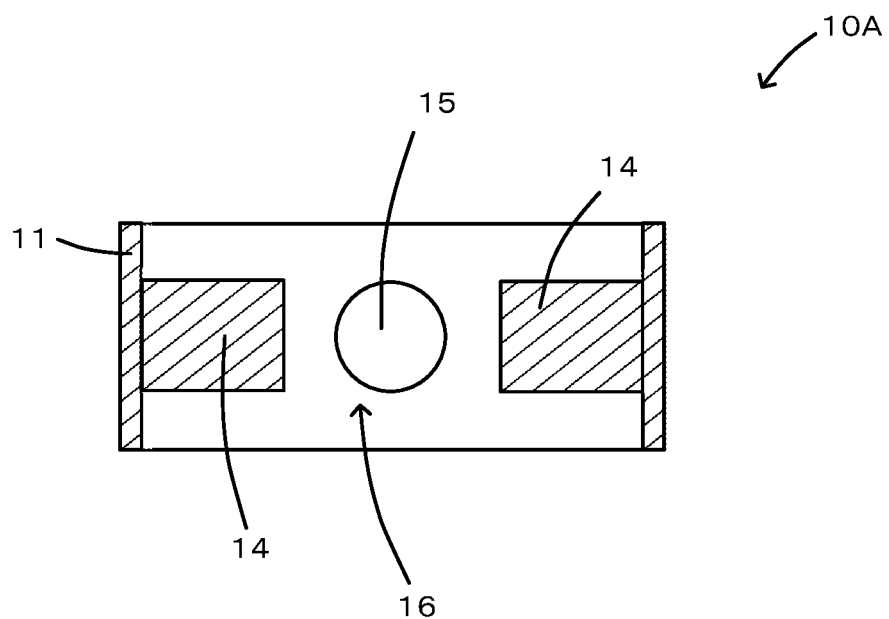

The rings 10 are not limited to those which have protrusions 12,13, as shown in FIGS. 2 A and 2 B, the rings 10A which have protrusions 14,15 having the structures as shown in FIGS. 3 A and 3 B, can be used.

In FIGS. 3 A and 3 B, the ring 10A is shown which has a protrusion 14 having a mountain shape at a section view and a protrusion 15 having a cylindrical shape. The protrusions are not limited to those having these structures, and can be those having various shapes.

The water treating method 1, the water treating apparatus 30 and the cavitation generation ring 10 of the first embodiment composed as mentioned above fine the clusters of molecules of the water 2 by a simple method.

That is to say, a fining process of the clusters is executed by cavitation generated inside the ring 10 by the cavitation generation ring 10, having the cylindrical portion 11 and the protrusions 12,13 having simple structures. Therefore, for example, a large-scale device structurally complicated like a magnetic field generation device etc. is not necessary and a fining process of the clusters with a simple method is fulfilled.

The Nano water 3 made in this way has a high permeation capability; the clusters being fined, the Nano water 3 is used in various ways, e.g., drinking water, hydroponics of plants, rearing of tropical fish, cosmetics related to beauty such as a skin lotion and cream.

In this embodiment, the water treating apparatus 30 has a plurality of rings 10 which are able to be connected to and separated from each other and the amount of cavitation generation is able to be adjusted by increasing or decreasing the number of the connected rings 10.

Therefore by changing the number of the connected rings 10, the degree of fining the clusters of the molecules of the water 2 is able to be adjusted, so the Nano water 3 which has a desired permeation capability is obtained according to the usage.

In this embodiment, each of the plurality of protrusions 12,13 of the ring 10 has a mushroom shape and has a combination of head portions 12*a*,13*a* in two or more different sizes. Therefore by combining the head portions 12*a*,13*a* in different sizes, the effect of cavitation is enhanced, so the water 2 having clusters in small sizes is produced effectively.

Next, a water treating method 1 A of the second embodiment is explained.

As shown in FIG. 1B, the water treating method 1A of this embodiment has a gas and liquid mixing step B for containing a lot of gas bubbles 5 in the water 2 by mixing gas 4 into the water communication pipe 20 to an upstream side of the cavitation generation ring 10.

As shown in FIG. 5 B, the water treating method 1A is executed by a water treating apparatus 30 A having a gas and liquid mixing apparatus 22.

In the gas and liquid mixing step B, cavitation is generated by passing the water 2 containing the gas bubbles 5 through the inside of the ring 10 at high pressure, thereby the clusters of molecules of the water 2 are fined, and the gas bubbles 5 are also fined to produce Nano bubbles 6 (gas bubbles fined in Nano-size).

Figure 4A:
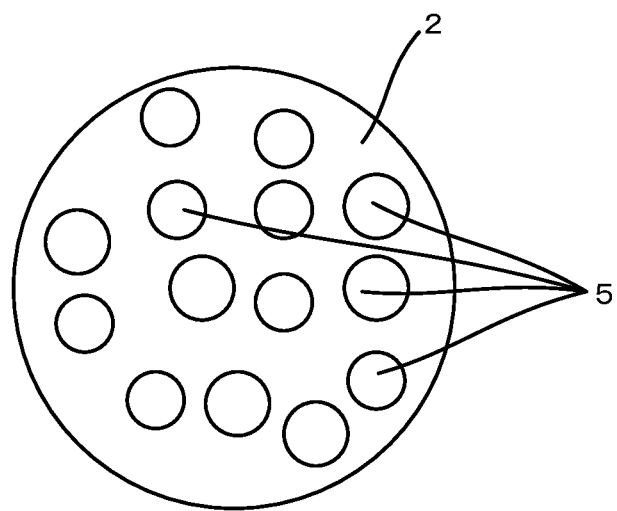
FIG. 4 A is a schematic view showing gas bubbles before cavitation treatment.
Figure 4B:
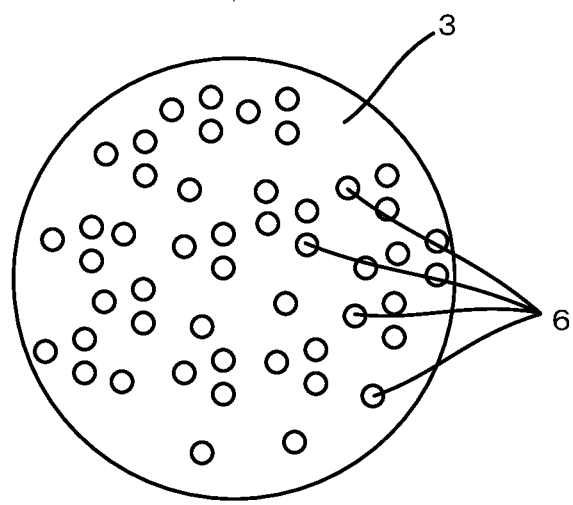

In FIG. 4 A, the gas bubbles 5 before being fined into Nano size, and in FIG. 4 B, the Nano bubbles 6 are shown. The size of the gas bubbles 5 is in a range from about 200 to 2000 micrometers and the size of the Nano bubbles 6 is in a range from about 100 to 500 micrometers.

By cavitation generated in the ring 10, vacuum microbubbles are generated in the water 2, and these vacuum microbubbles collide with the gas bubbles 5 generated in the water 2, then the gas bubbles 5 are instantly collapsed (fined) into the Nano bubbles 6.

By increasing the amount of cavitation generation by appropriately increasing the number of the connected rings 10, and by enhancing the effect of cavitation by combining the head portions 12*a*,13*a* in different sizes, an acute adiabatic compression reaction occurs at the timing of the above mentioned collapse of the gas bubbles 5, and a super high pressure, high temperature extreme reaction field is formed in the Nano bubbles 6.

Thus, the water molecules around the Nano-bubbles 6 are broken down and free radicals such as OH are generated or ozones are generated from part of the oxygen in the gas bubbles 5.

The free radicals and the ozones generated like this have a strong oxidizing effect, therefore the water after the treatment has a sterilization effect and a deodorization effect etc., so it is used for a sewage treatment or a decomposition of contaminated water etc.

In this embodiment, as shown in FIG. 1 B, the water treatment 1 A further includes a negatively ionizing step C for passing the water 2 which contains the Nano bubbles 6 through the inside of the magnetic mixer 23, thereby the Nano bubbles 6 being negatively ionized.

In this negatively ionizing step C, as shown in FIG. 5 B, while the water 2 containing the Nano bubbles 6 passes through the magnetic mixer 23, negative ions are attached onto the surface of the Nano bubbles 6. Thereby, negative ions repulse each other, and the Nano bubbles 6 become hard to attach each other, which avoids an increase of the size of the Nano bubbles 6 caused by a plurality of Nano bubbles 6 being merged, and which maintains the size of the Nano bubbles 6 in Nano level.

As the magnetic mixers 23, those which attach negative ions onto the surface of Nano bubbles 6 can be used, and those having various structures can be used.

The water treating method 1 A (the water treating apparatus 30 A) of the second embodiment, composed as mentioned above, has a gas and liquid mixing step B (a gas and liquid mixing apparatus 22) for containing a lot of gas bubbles 5 in the water 2 by mixing the gas 4 into the water communication pipe 20 to an upstream side of the cavitation generation ring 10.

Therefore, by cavitation generated by passing the water 2 containing gas bubbles 5 through the inside of the ring 10 at high pressure, the clusters of molecules of the water 2 are fined and also the gas bubbles 5 are fined into Nano size to generate the Nano bubbles 6.

Thus, the Nano bubbles 6 are kept in the water 2, so various gases (nitrogen gas, carbon dioxide, oxygen gas, etc.) are kept in water as the Nano bubbles 6 according to the usage.

And cavitation is generated by increasing the amount of cavitation generation by increasing the number of the connected rings 10 appropriately, and by enhancing the effect of cavitation by combining the head portions 12a,13a having different sizes. Thereby, the water molecules around the Nano bubbles 6 are broken down and free radicals such as OH are generated, or ozones are generated from part of oxygen in the gas bubbles 5. The free radicals and ozones generated like this have a strong oxidizing effect, so the Nano water 3 after the treatment has a sterilization effect and a deodorization effect etc., which is used for a sewage treatment etc.

In this embodiment, the water treating method 1 A further includes the negatively ionizing step C for passing the water 2 which contains the Nano bubbles 6 fined in Nano size by cavitation generated in the ring 10 through the inside of the magnetic mixer 23, thereby the Nano bubbles 6 are negatively ionized.

Therefore, the Nano bubbles 6 are negatively ionized, and the Nano bubbles 6, 6 become hard to attach each other, which avoids an increase of the size of the Nano bubbles 6 caused by a plurality of Nano bubbles 6 being merged, thereby the Nano bubbles 6 are effectively contained in the water 2.

Next, the water treatment method 1 B of the third embodiment is explained.

As shown in FIG. 1 C, the water treatment method 1 B has a fine particles mixing step D for mixing and dispersing fine particles 7 in Nano-size in the gas 4 in the gas and liquid mixing step B, before the gas 4 is mixed into the water 2.

As shown in FIG. 5 C, the water treating method 1 B is executed by the water treating apparatus 30 B which has an apparatus for mixing fine particles 24. The method 1 B (the water treating apparatus 30 B) has a negatively ionizing step C (a magnetic mixer 23), like above second embodiment.

In the fine particles mixing step D, the gas 4 into which the fine particles 7 are mixed to be dispersed is mixed into the water 2 in the gas and liquid mixing process B, then the gas bubble 5 containing the fine particles 7 are produced.

The water 2 which contains the gas bubbles 5 including the fine particles 7 passes through the inside of the ring 10 at high pressure, then cavitation is generated, thereby the clusters of molecules of the water 2 are fined and also the gas bubbles are fined into Nano size in such a manner that the fine particles 7 are enclosed inside the Nano bubbles 6.

The size of the fine particles 7 is set so that the fine particles 7 are enclosed in the Nano bubbles 6, and the size is smaller than the Nano bubbles 6, for example, it can be set to be in a range from about 100 to 500 nanometers.

As the fine particles 7, those which are made by drying and powdering an extract of stevia stem and fining the powdered extract in Nano-size are used. The Nano water 3 containing the Nano bubbles 6 in which the fine particles are enclosed inside are used for a fertilizer for hydroponics of plants and the Nano water 3 has effects of increasing a sugar content rate of fruits and improving a growth of plants.

As the method for drying and powdering an extract of stevia stem, for example, the method below is used. First of all, a stevia stem is dried by natural drying etc., and this dried one is broken into pieces to obtain powder of the stevia stem, then the powder of the stevia stem is boiled to obtain extract solution. Then, the extracted solution is concentrated in a vacuum condition and the concentrated solution becomes mature after the first fermentation, thereby stevia extract is obtained. This is a method for drying and powdering the stevia extract and fining the powdered extract into Nano size.

The stevia extract is used for a growth promoter for a useful microorganism and a nutritive feed additive for raising domestic animals, such as chicken, and aquarium fish, in addition to a fertilizer for hydroponics of plants. It is also used for a wide range of purposes, such as for an active ingredient for health foods and various cosmetic, such as a skin lotion and cream. This stevia extract is diluted with the Nano water 3 to some proper concentration rate before usage.

As the fine particles 7, those which are hydrophilic or hydrophobic are used. When the hydrophobic particles are dissolved in the water 2, even if they are fined, they are hard to be dispersed in the water 2. However, since this method enables the fine particles 7 to be enclosed in the Nano bubble 6, even if they are hydrophobic, they are dispersed in the water 2.

Grinding machines of various structures can be used for fining fine particles 7 in Nano size.

The water treating method 1 B (the water treating apparatus 30 B) of the third embodiment, composed as mentioned above, further includes the fine particles mixing step D (the apparatus for mixing fine particles 24) for mixing and dispersing the fine particles 7 in Nano-size in the gas 4 in the gas and liquid mixing step B, before the gas 4 is mixed into the water 2. Therefore, various kinds of the fine particles 7 are enclosed in the Nano bubbles 6, and are contained in the water 2. So, for example, even fat-soluble fine particles 7 are enclosed in the Nano bubbles 6, and are contained in water 2.

Since the size of the fine particles 7 which are contained in the Nano water 3 after treatment is in Nano size, the fine particles 7 are effectively absorbed via cell surface etc., which exhibits a great effect of the fine particles 7.

For example, in case of using the fine particles 7 which promote a growth of plants etc., the effect of increasing a sugar content rate of fruits or a promotion of the growth of plants is brought about relatively certainly.

Next, the experimental results are shown below regarding a permeation capability of the Nano water 3 which is produced by the water treating method 1 and the water treating apparatus 30.

(Experiments for the Precipitation of Felt Cloths)

Purpose: To compare a permeation capability of the Nano water 3 with that of tap water.

Method: The felt clothing was cut into multiple square pieces, and these pieces were made to float on the surface of the Nano water 3 stored in a cup, then the time (time for permeation) between the point of floating and the point where the pieces started precipitating was measured. Tap water was used as an object for this experiment.

Results:

TABLE 1

| | Pieces of felt used | Nano water 3 | Tap water | |
|---|---|---|---|---|
| The first time | 2.9 cm * 2.8 cm * 1 mm | 9" 78 seconds | 3 minutes or over | Time for permeation |
| The second time | 3.0 cm * 2.5 cm * 1 mm | 15" 36 minutes | 36" 51 seconds | |
| The third time | 2.5 cm * 2.9 cm * 1 mm | 55" 06 seconds | 3 minutes or over | |

For all of three times, the Nano water 3 has a longer permeation time than tap water.

Analysis: As is shown above, the Nano water 3 permeates into the inside of the felt clothing in a shorter time than tap water, therefore it is suggested that the Nano water 3 has a greater permeation capability than tap water.

Next, the experimental results are shown regarding the growth promotion effect of stevia extract for plants, which is diluted with the Nano water 3.

(Experiments Regarding the Growth Promotion Effect of Stevia Extract for Plants)

Purpose: To know if the stevia extract which is diluted with the Nano water 3 has an effect of promotion of growth of plants.

(Test section) Stevia extract was diluted by about 2000 times with the Nano water 3. This diluted stevia extract was sprayed on the surface of the leaves of green onion in the course of their growth four times with seven days intervals. The spraying amount of the diluted stevia extract was two liters every four beds (23 meters/bed).

(Target section) Stevia extract diluted with the Nano water 3 was not sprayed on the leaves of green onion.

Results:

TABLE 2

| | Yield of green onion |
|---|---|
| Test section | 7 kg * 30 containers per bed |
| Target section | 7 kg * 25 containers per bed |

As mentioned above, it was confirmed that the test section has a larger yield of green onion than the target section. Moreover, it was confirmed that the test section had a larger weight of the harvested green onion and had a faster growth speed of green onion than the target section.

Analysis: It is suggested that the stevia extract which is diluted with the Nano water 3 has an effect of promoting the growth of plants. Also it is suggested that since the Nano water 3 has a high permeating capability, stevia extract is effectively absorbed via cell surfaces of green onion.

The water treating method 1, 1A, 1B (the water treating apparatus 30, 30A, 30B) in the above embodiments is not limited to an embodiment which is executed individually. Any of them can be executed by being combined with any others. For example, for the water which is treated by the water treating method 1 (the water treating apparatus 30) of the first embodiment, the treatment of the water treatment method 1 A (the water treatment apparatus 30 A) of the second embodiment can be executed, or for this treated water, the treatment of the water treatment method 1 B (the water treatment apparatus 30 B) can be executed.

Thereby, since the treated water experiences a fining process A for multiple times, it is strongly affected by effect of cavitation and the clusters are fined effectively and Nano bubbles are easily generated.

REFERENCE SIGNS LIST 1,1A,1B water treating method
B gas and liquid mixing step
C negatively ionizing step
D fine particles mixing step
2 water
4 gas
5 gas bubbles
6 gas bubbles (Nano bubble)
7 fine particles
10,10A cavitation generation ring (ring)
11 cylindrical portion
12,13,14,15 protrusion
12a,13a head portion
16 water communication path
20 water communication pipe
21 pressurizing pump
22 gas and liquid mixing apparatus
24 apparatus for mixing fine particles
30,30A,30B water treating apparatus

The invention claimed is:

1. A water treating method, comprising:
installing a cavitation generation ring in a part of a water communication pipe, the cavitation generation ring having a cylindrical portion and a plurality of protrusions, inside the cylindrical portion a water communication path being formed, the plurality of protrusions protruding toward a center from an inner peripheral surface of the cylindrical portion;
passing water through the inside of the cylindrical portion at high pressure, thereby cavitation being generated in the cylindrical portion and clusters of molecules of water being fined;
a gas and liquid mixing step for containing a lot of gas bubbles in the water by mixing a gas into the water communication pipe to an upstream side of the cavitation generation ring; and
a fine particles mixing step for mixing and dispersing fine particles in Nano-size in the gas and liquid mixing step, before the gas is mixed into the water, thereby the fine particles being enclosed in the gas bubbles fined in Nano-size,
wherein cavitation is generated in the cylindrical portion by passing the water containing the gas bubble through the inside of the cylindrical portion at high pressure, thereby the clusters of molecules of the water are fined and also the gas bubbles are fined in Nano-size.

2. The water treating method as set forth in claim 1, wherein the fine particles are made by drying and powdering an extract of stevia stem and fining the powdered extract in Nano-size.

3. The water treating method as set forth in claim 2, further comprising a negatively ionizing step for having the water which contains the gas bubbles fined in Nano-size by the cavitation pass through the inside of a magnetic mixer, thereby the gas bubbles being negatively ionized.

4. The water treating method as set forth in claim 1, further comprising a negatively ionizing step for having the water which contains the gas bubbles fined in Nano-size by the cavitation pass through the inside of a magnetic mixer, thereby the gas bubbles being negatively ionized.

5. A water treating apparatus, comprising:
a cavitation generation ring configured to be installed in a part of a liquid communication pipe, comprising a cylindrical portion and a plurality of protrusions, inside the cylindrical portion a water communication path being formed, the plurality of protrusions protruding toward a center from an inner peripheral surface of the cylindrical portion, wherein water is made to pass through the inside of the cylindrical portion at high pressure, thereby cavitation is generated in the cylindrical portion and clusters of molecules of the water are fined and gas bubbles contained in the water are fined in Nano-size;
a water communicating pipe;
a pressurizing pump for water;
a gas and liquid mixing apparatus for containing a lot of gas bubbles in the water by mixing gas into the water communication pipe to an upstream side of the cavitation generation ring; and
an apparatus for mixing fine particles, the apparatus mixing and dispersing fine particles in Nano-size in the gas, before the gas is mixed into the water by the gas and liquid mixing apparatus.

6. The water treating apparatus as set forth in claim 5, wherein the fine particles are made by drying and powdering an extract of stevia stem and fining the powdered extract in Nano-size.

7. The water treating apparatus as set forth in claim 6, comprising:
a plurality of the cavitation generation rings which are able to be mutually connected to and separated from, wherein amount of cavitation generation is able to be adjusted by increasing or decreasing a number of the connected cavitation generation rings.

8. The water treating apparatus as set forth in claim 5, comprising:
a plurality of the cavitation generation rings which are able to be mutually connected to and separated from, wherein amount of cavitation generation is able to be adjusted by increasing or decreasing a number of the connected cavitation generation rings.

9. The water treating apparatus as set forth in claim 5, wherein each of the plurality of protrusions of the cavitation generation rings has a mushroom shape and the cavitation generation ring has a combination of head portions in two or more different sizes.

10. A water treating method, comprising:
installing a cavitation generation ring in a part of a water communication pipe, the cavitation generation ring having a cylindrical portion and a plurality of protrusions, inside the cylindrical portion a water communication path being formed, the plurality of protrusions protruding toward a center from an inner peripheral surface of the cylindrical portion;
passing water through the inside of the cylindrical portion at high pressure, thereby cavitation being generated in the cylindrical portion and clusters of molecules of water being fined;
a gas and liquid mixing step for containing a lot of gas bubbles in the water by mixing a gas into the water communication pipe to an upstream side of the cavitation generation ring; and
wherein cavitation is generated in the cylindrical portion by passing the water containing the gas bubble through the inside of the cylindrical portion at high pressure, thereby the clusters of molecules of the water are fined and also the gas bubbles are fined in Nano-size, wherein each of the plurality of protrusions of the cavitation generation rings has a mushroom shape and the cavitation generation ring has a combination of head portions in two or more different sizes.

11. A water treating apparatus, comprising:
a cavitation generation ring configured to be installed in a part of a liquid communication pipe, comprising a cylindrical portion and a plurality of protrusions, inside the cylindrical portion a water communication path being formed, the plurality of protrusions protruding toward a center from an inner peripheral surface of the cylindrical portion, wherein water is made to pass through the inside of the cylindrical portion at high pressure, thereby cavitation is generated in the cylindrical portion and clusters of molecules of the water are fined and gas bubbles contained in the water are fined in Nano-size;
a water communicating pipe;
a pressurizing pump for water; and
a gas and liquid mixing apparatus for containing a lot of gas bubbles in the water by mixing gas into the water communication pipe to an upstream side of the cavitation generation ring,
wherein each of the plurality of protrusions of the cavitation generation rings has a mushroom shape and the cavitation generation ring has a combination of head portions in two or more different sizes.

* * * * *